United States Patent [19]

Lenselink et al.

[11] 4,219,449

[45] Aug. 26, 1980

[54] CARANE NITRILES

[75] Inventors: Willem Lenselink, Voorthuizen; Dirk K. Kettenes, Putten, both of Netherlands

[73] Assignee: Polak's Frutal Works B.V., Amersfoort, Netherlands

[21] Appl. No.: 879,019

[22] Filed: Feb. 17, 1978

[30] Foreign Application Priority Data

Mar. 23, 1977 [GB] United Kingdom ............... 12223/77

[51] Int. Cl.[3] ...................... A61K 7/46; C07C 121/47; C07C 121/48

[52] U.S. Cl. ................................ 252/522 R; 260/464

[58] Field of Search ......................... 252/522; 260/464

[56] References Cited

U.S. PATENT DOCUMENTS

| | | | |
|---|---|---|---|
| 3,168,550 | 2/1965 | Blumenthal | 260/464 |
| 3,530,171 | 9/1970 | Heckert | 252/522 X |
| 3,531,510 | 9/1970 | Blumenthal | 252/522 X |
| 3,627,815 | 12/1971 | Hall, Jr. | 260/464 |
| 3,686,097 | 8/1972 | Kropp | 252/522 |
| 3,714,220 | 1/1973 | Dahill, Jr. | 252/522 X |
| 3,869,493 | 3/1975 | Bozzato et al. | 252/522 X |
| 3,928,247 | 12/1975 | Mookherjee et al. | 260/464 X |

*Primary Examiner*—Joseph Paul Brust
*Attorney, Agent, or Firm*—William S. Alexander

[57] ABSTRACT

Novel nitriles are disclosed based on the structure of 3,7,7-trimethylbicycloheptane. These compounds are disclosed and shown to be useful as ingredients in perfume compositions.

38 Claims, No Drawings

CARANE NITRILES

This invention relates to new chemical compounds useful as perfumes or as components of perfumes. Specifically it relates to nitriles based on the skeleton of carane, i.e. 3,7,7-trimethylbicyclo{4.1.0}heptane.

In recent years a trend in perfumery is observable in the direction of the use of nitriles, which class of compounds has previously been rather unexploited for perfumery purposes. Besides the desirable olfactory properties of the nitriles for modern perfumery, most of the nitriles which have to date found acceptance in perfumery also possess desirable properties with respect to chemical stability and resistance to discolouration in many applications, e.g. in soap and other cosmetic preparations, where many otherwise useful perfumery chemicals are not stable. In particular 3,7-dimethyl-6-octenenitrile, 3,7-dimethyl-2,6-octadienenitrile and also 3-phenylacrylonitrile are useful in perfumery.

It is the object present invention to provide a novel class of nitriles based on the carbon skeleton of 3,7,7-trimethylbicyclo [4.1.0]heptane. These novel nitriles are represented by the general formulae I and II wherein the dotted lines represent carbon-to-carbon double or single bonds subject to the limitation that

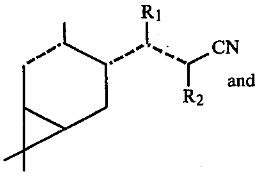
and
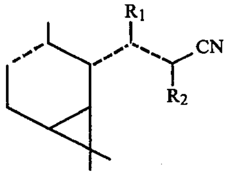

I II in the nitrile containing chain only one dotted line can be double bond, and $R_1$ and $R_2$ represent hydrogen or alkyl radicals of 1 to 6 carbon atoms, and the total carbon number of $R_1+R_2$ is 6 or less. Hereinafter, for the sake of convenience, the novel class of nitriles will sometimes be referred to collectively by the general formula

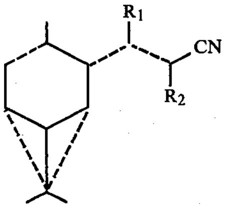

III to indicate the alternate configurations of the bridgehead carbon atoms.

Examplary, but by no means all, compounds of the invention having the specified structure are:

3(3,7,7-trimethylbicyclo {4.1.0}-heptyl-2)acrylonitrile
3(3,7,7-trimethylbicyclo {4.1.0}-heptyl-4)acrylonitrile
3(3,7,7-trimethylbicyclo {4.1.0}-heptylidene-2) propanenitrile
3(3,7,7-trimethylbicyclo {4.1.0}-heptylidene-4)propanenitrile
2-methyl-3-(3,7,7-trimethylbicyclo {4.1.0}-heptyl-2)-acrylonitrile
2-methyl-3(3,7,7-trimethylbicyclo {4.1.0}-heptylidene-4)propanenitrile
2-hexyl-3(3,7,7-trimethylbicyclo {4.1.0}-heptyl-2)acrylonitrile
2-hexyl-3(3,7,7-trimethylbicyclo {4.1.0}-heptyl-4)acrylonitrile
2-hexyl-3(3,7,7-trimethylbicyclo {4,1.0}-heptylidene-2)propanenitrile
3-(3,7,7-trimethylbicyclo {4.1.0}-2-heptenyl-4)-2-butenenitrile
3-(3,7,7-trimethylbicyclo {4.1.0}-heptyl-4)-2-pentenenitrile It will be apparent that the novel nitriles can exist in a wide variety of positional and stereoisomeric forms and it is intended that these be included within the structural formulae. The starting material for the novel nitriles of the invention is either 2-carene, i.e. 3,7,7-trimethylbicyclo {4.1.0}-heptane-2 or 3-carene, i.e. 3,7,7-trimethylbicyclo {4.1.0}-heptane-3. Both of these isomers are optically active and occur in nature in both their d- and l-forms or as d,l-mixtures. The 3-carene, and in particular (+)-3-carene, is readily available from natural sources and is plentiful and relatively inexpensive and is accordingly attractive as a starting material. The novel nitriles can be prepared by methods known to the art.

In a preferred method an oxo-compound of the general formula

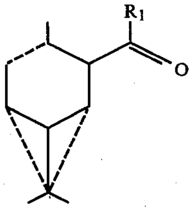

IV wherein the dashed lines and $R_1$ are as described above, is reacted with a nitrile group-containing reagent, for example, cyanoacetic acid and its esters, a cyclonalkyl phosphonate or an alkylnitrile. The oxo-compound represented by formula IV can be prepared from d-, 1-, or d,l-forms of 2-carene or 3-carene by methods known to the art. Direct hydroformylation using a method taught by Falbe, Synthesen mit Kohlenmonoxyde, Springer Verlag, Berlin (1967), pages 3-72, leads to mixtures of 2- and 4-formyl caranes. This is a preferred method of preparing compounds wherein $R_1$ is hydrogen.

Another preferred method of preparing the oxo-compound is by direct acylation of the carene using the method taught by Muhlstadt et al., in East German patent nr. 68903 and in Chem. Ber. 100, p. 1892 (1967). When using this method, the product retains a C—C double bond, which can be hydrogenated or not, as desired, before the acylated product is converted to a nitrile. This method is also advantageous in that the reaction is selective in reacting at the original double bond, thus leading predominantly to substitution at the 2 position with 2-carene and at the 4 position with 3-carene.

An indirect method of preparing the oxo-compound is by way of the Prins reaction of alkenes with alkenes with aldehydes using the method taught by Roberts in Olah, Friedel-Crafts and Related Reactions, vol. 3, Interscience Publishers, Inc., New York, 1964, pages 1175–1210, and specifically for 3-carene by Ohloff et al., Ann. 613, p. 43 (1958). By this method it is also possible to prepare a product which retains a C—C double bond, which can be hydrogenated if desired and the reaction also takes place specifically at the double bond. As stated above, the nitriles of this invention are preferably prepared by reacting an oxo-compound of the formula shown above with a reagent containing a nitrile group. One method known for this reaction is the Knoevenagel condensation of the oxo-compound with cyanoacetic acid or esters thereof — cf.G. Jones in Organic Reactions, John Wiley and Sons, Inc., New York, 1967, volume 15, p. 236–244 - followed by decarboxylation.

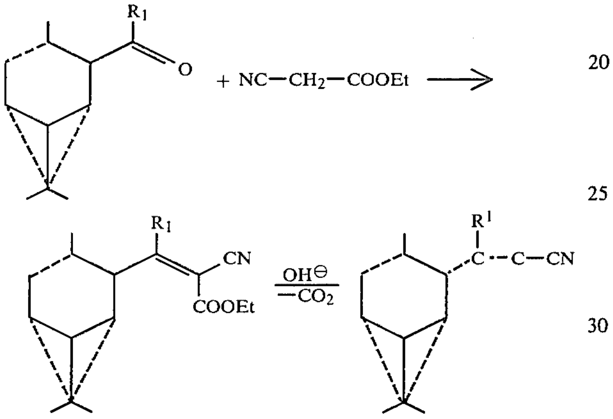

The decarboxylation of the intermediate substituted cyanoacetic acid can be influenced by the reaction conditions employed, such as solvents, added chemicals etc. The decarboxylation step can be performed by simple heating of the intermediate alkylidene cyanoacetic acids, but it preferably carried out with the help of nitrogen bases such as pyridine, pyrimidine, morpholine, piperidine, triethanolamine, dimethylformamide and the like. Well known decarboxylation catalysts such as copper compounds, for example $Cu_2O$ as taught by Fairhurst, Horwell and Timms, Tetrahedron Letters 1975, p. 3843 can also be used. The condensation products of the oxo-compound with cyanoacetic esters can be saponified and decarboxylated simultaneously by treating with water in the presence of dimethylformamide or dimethylsulfoxide as described by Krapcho, Jahngen and Lovey, Tetrahedron Letters, 1973, p. 957 and 1974, p. 1091.

Nitriles of the invention with saturated nitrogen containing side chains, can conveniently be prepared via a simultaneous condensation-reduction method by performing the condensation of the oxo-compound with cyanoacetic esters in a hydrogen atmosphere and a hydrogenation catalyst as described by Alexander and Cope, J.Am.Chem.Soc. 66, p. 886 (1944).

It will be apparent that the condensation of the oxo-compounds with cyanoacetic acid or esters, followed by decarboxylation leads to nitriles of the invention represented by the general formula I or II in which $R_2$ is hydrogen. According to the invention it is possible to introduce an alkyl group R by direct alkylation of the intermediate alkylidenecyanoacetic ester. This alkylation is preferably carried out by the application of a strong base such as sodium hydride in an aprotic solvent such as dimethylformamide and an alkylhalide, RX, wherein X can be chloride, bromine or iodine and R is lower alkyl fitting the description of the alkyl groups encompassed by $R_2$ above.

Saponification and subsequent decarboxylation of the resulting disubstituted cyanoacetic ester leads to nitriles of the invention in which $R_2$ is an alkyl radical. The reaction sequence can be represented as follows:

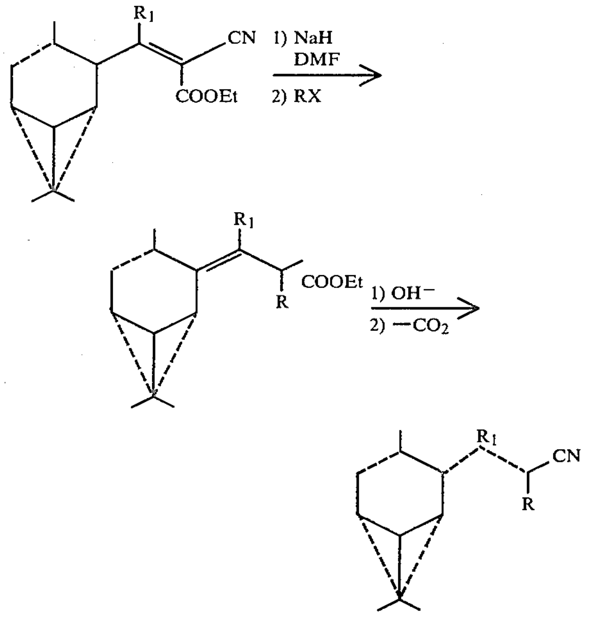

Another preferred method of the preparation of the nitriles of the invention is via the Wittig-reaction of the oxo-compounds with a cyanoalkylphosphonate in the presence of a base, for example, with $(EtO)_2$-$POCHR_2CN$ as described in the German patent 1.108.208. Also useful is the two phase modification of this reaction according to Piechucki, Synthesis 1974, p. 869 and to D'Incan and Seyden-Penne, Synthesis 1975, p. 516. The reaction is set forth in the following scheme:

IV

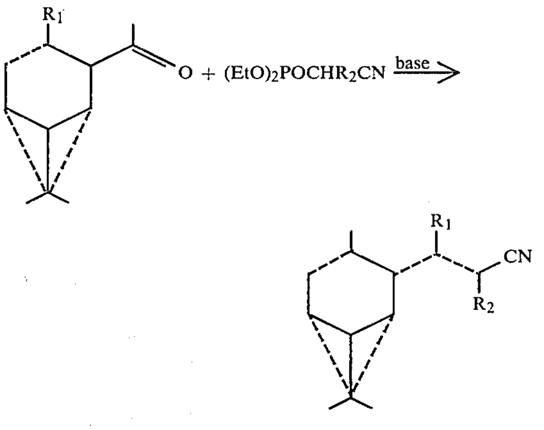

III

The oxo-compounds can also be condensed directly with alkylnitriles in the presence of an alkaline catalyst such as KOH. However this method is less attractive due to inferior yields in comparison with the other methods. Furthermore, some of the oxo-compounds, especially the aldehyde, are not sufficiently stable under the reaction conditions employed.

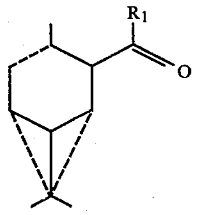

IV

+ $R_2CH_2$—CN base

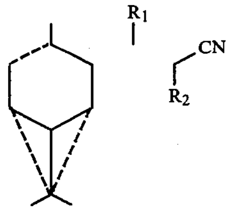

III

Depending on the starting material and the reaction procedure employed, the nitriles of the invention can exist in a variety of positional and stereoisomeric forms. Since the preferred starting material, 3-carene, exists in a d- and l-optical configuration the same result can be expected in the oxo-compounds prepared from them. Moreover in the case of hydroformylation of, e.g., 3-carenes substitution can result at either the 2-or 4-position. Thus there results a possibility of eight 2-formylcaranes and eight 4-formylcaranes resulting from hydroformylation of a d,l-mixture of 3-carenes. These are represented by the following structural formulae:

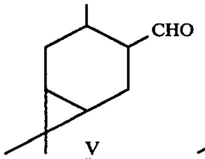

V

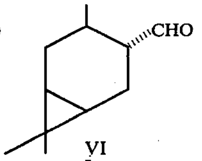

VI

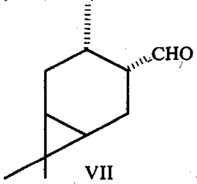

VII

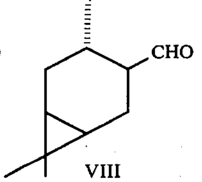

VIII

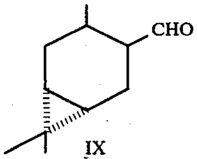

IX

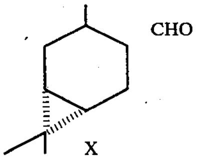

X

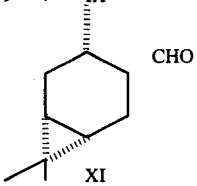

XI

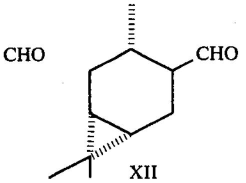

XII

-continued

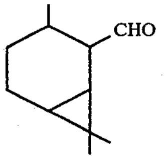

XIII

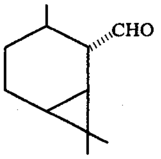

XIV

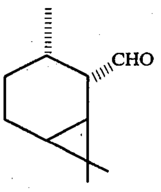

XV

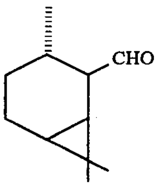

XVI

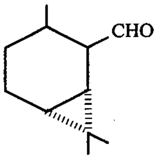

XVII

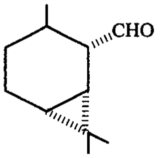

XVIII

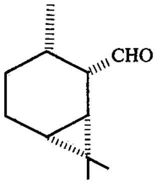

IXX

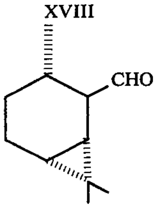

XX

It will be apparent, as shown by the general formulae, that the nitriles of the invention which possess a double bond in the nitrogen-containing side chain, can exist in two isomeric forms with respect to the position of the double bond relative to the nitrile group. This position can either be $\alpha,\beta$ or $\beta,\gamma$-to the nitrile group. Furthermore in either of these positions, double bonds can exist in an E- or Z-configuration, so that a total of 4 isomeric nitriles, represented by the formula's XXI - XXIV, are possible with respect to the location and configuration of the double bond in the nitrile group containing side chain:

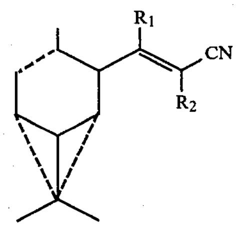

XXI

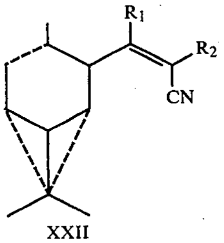

XXII

-continued

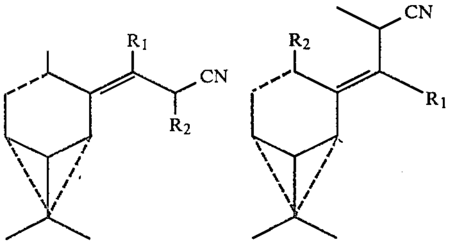

XXIII XXIV

It will further be apparent that the compounds of the invention can exist in various stereoisomeric and enantiomorphs forms with respect to the substituents on the cyclohexane ring, depending on their place in the cyclohexane ring and on their orientation relative to the plane of the cyclohexane ring.

This can be illustrated by the reaction product of the cyanoacetic ester synthesis using formyl carane from d,1-3-carene.

As stated above, there is a possibility of a mixture of 16 formylcaranes, V - XX, on hydroformylation of the d,1-3-carene. Such a mixture, reacted with cyanoacetic acid followed by decarboxylation, yields a mixture which can contain 24 isomeric nitriles and 24 enanthiomorphs thereof.

The resulting 48 possible compounds are as follows:

(E)-3-((IS, 3R, 4R)-3,7,7-trimethylbicyclo {4.1.0}-heptyl-4)acrylonitrile (E)-3-((1R, 3R, 4R)-3,7,7-trimethylbicyclo {4.1.0}-heptyl-4-)acrylonitrile (E) -3-((1S, 3S, 4R)-3,7,7-trimethylbicyclo {4.1.0}-heptyl-4-)acrylonitrile (E) -3-((1R, 3S, 4R)-3,7,7-trimethylbicyclo {(4.1.0}-heptyl-4-)acrylonitrile (E) -3-((1S, 3R, 4S)-3,7,7-trimethylbicyclo {4.1.0}-heptyl-4-)acrylonitrile (E) -3-((1R, 3R, 4S)-3,7,7-trimethylbicyclo {4.1.0}-heptyl-4-)acrylonitrile (E) -3-((1S, 3S, 4S)-3,7,7-trimethylbicyclo {4.1.0}-heptyl-4-)acrylonitrile (E) -3-((1R, 3S, 4S)-3,7,7-trimethylbicyclo {4.1.0}-heptyl-4-)acrylonitrile (Z) -3-((1S, 3R, 4R)-3,7,7-trimethylbicyclo {4.1.0}-heptyl-4-)acrylonitrile (Z) -3-((1R, 3R, 4R)-3,7,7-trimethylbicyclo {4.1.0}-heptyl-4-)acrylonitrile (Z) -3-((1S, 3S, 4R)-3,7,7-trimethylbicyclo {4.1.0}-heptyl-4-)acrylonitrile (Z) -3-((1R, 3S, 4R)-3,7,7-trimethylbicyclo {4.1.0}-heptyl-4-)acrylonitrile (Z)-3-((1S, 3R, 4S)-3,7,7-trimethylbicyclo{4.1.0}-heptyl-4-)acrylonitrile (Z)-3-((1R, 3R, 4S)-3,7,7-trimethylbicyclo{4.1.0}-heptyl-4-)acrylonitrile (Z)-3-((1S, 3S, 4S)-3,7,7-trimethylbicyclo{4.1.0}-heptyl-4-)acrylonitrile (Z)-3-((1R, 3S, 4S)-3,7,7-trimethylbicyclo{4.1.0}-heptyl-4-)acrylonitrile (E)-3-((1R, 2S, 3R)-3,7,7-trimethylbicyclo{4.1.0}-heptyl-2-)acrylonitrile (E)-3-((1S, 2S, 3R)-3,7,7-trimethylbicyclo{4.1.0}-heptyl-2-)acrylonitrile (E)-3-((1R, 2S, 3S)-3,7,7-trimethylbicyclo{4.1.0}-heptyl-2-)acrylonitrile (E)-3-((1S, 2S, 3S)-3,7,7-trimethylbicyclo{4.1.0}-heptyl-2-)acrylonitrile (E)-3-((1R, 2R, 3R)-3,7,7-trimethylbicyclo{4.1.0}-heptyl-2-)acrylonitrile (E)-3-((1S, 2R, 3R)-3,7,7-trimethylbicyclo{4.1.0}-heptyl-2-)acrylonitrile (E)-3-((1R, 2R, 3S)-3,7,7-trimethylbicyclo{4.1.0}-heptyl-2-)acrylonitrile (E)-3-((1S, 2R, 3S)-3,7,7-trimethylbicyclo{4.1.0}-heptyl-2-)acrylonitrile (Z)-3-((1R, 2S, 3R)-3,7,7-trimethylbicyclo{4.1.0}-heptyl-2-)acrylonitrile (Z)-3-((1S, 2S, 3R)-3,7,7-trimethylbicyclo{4.1.0}-heptyl-2-)acrylonitrile (Z)-3-((1R, 2S, 3S)-3,7,7-trimethylbicyclo{4.1.0}-heptyl-2-)acrylonitrile (Z)-3-((1S, 2S, 3S)-3,7,7-trimethylbicyclo{4.1.0}-heptyl-2-)acrylonitrile (Z)-3-((1R, 2R, 3R)-3,7,7-trimethylbicyclo{4.1.0}-heptyl-2-)acrylonitrile (Z)-3-((1S, 2R, 3R)-3,7,7-trimethylbicyclo{4.1.0}-heptyl-2-)acrylonitrile (Z)-3-((1R, 2R, 3S)-3,7,7-trimethylbicyclo{4.1.0}-heptyl-2-)acrylonitrile (Z)-3-((1S, 2R, 3S)-3,7,7-trimethylbicyclo{4.1.0}-heptyl-2-)acrylonitrile (E)-3-((1S, 3R)-3,7,7-trimethylbicyclo{4.1.0}-heptylidene-4)propanenitrile (E)-3-((1R, 3R)-3,7,7-trimethylbicyclo{4.1.0}-heptylidene-4-) propanenitrile (E)-3-((1S, 3S)-3,7,7-trimethylbicyclo{4.1.0}-heptylidene-4-) propanenitrile (E)-3-((1R, 3S)-3,7,7-trimethylbicyclo{4.1.0}-heptylidene-4-)propanenitrile (Z)-3-((1S, 3R)-3,7,7-trimethylbicyclo{4.1.0}-heptylidene-4-)propanenitrile (Z)-3-((1R, 3R)-3,7,7-trimethylbicyclo{4.1.0}-heptylidene-4-) propanenitrile (Z)-3-((1S, 3S)-3,7,7-trimethylbicyclo{4.1.0}-heptylidene-4-)propanenitrile (Z)-3-((1R, 3S)-3,7,7-trimethylbicyclo{4.1.0}-heptylidene-4-)propanenitrile (E)-3-((1S, 3R)-3,7,7-trimethylbicyclo{4.1.0}-heptylidene-2-) propanenitrile (E)-3-((1R, 3R)-3,7,7-trimethylbicyclo{4.1.0}-heptylidene-2-)propanenitrile (E)-3-((1S, 3S)-3,7,7-trimethylbicyclo{4.1.0}-heptylidene-2-) propanenitrile (E)-3-((1R, 3S)-3,7,7-trimethylbicyclo{4.1.0}-heptylidene-2-) propanenitrile (Z)-3-((1S, 3R)-3,7,7-trimethylbicyclo{4.1.0}-heptylidene-2-)propanenitrile (Z)-3-((1R, 3R)-3,7,7-trimethylbicyclo{4.1.0}-heptylidene-2-) propanenitrile (Z)-3-((1S, 3S)-3,7,7-trimethylbicyclo{4.1.0}-heptylidene-2-)propanenitrile (Z)-3-((1R, 3S)-3,7,7-trimethylbicyclo{4.1.0}-heptylidene-2-)propanenitrile The ratio of nitrile isomers formed can be influenced by the reaction conditions employed and by the choice of starting material with respect to, for example, the optical configuration and substitution pattern at the cyclohexane ring. According to the invention it was found that in the above mentioned Wittig-type reactions of the oxo-compounds with cyanoalkyl phosphonates predominantly the isomers with α, β-unsaturated nitrile side chains are formed. The E/Z ratio of the double bond in the nitrile group containing side chain can be influenced to a certain extent by the solvent-base combination employed in this reaction. Aprotic conditions favor a higher content of Z-isomers than do protic conditions. The formation of $\beta,\gamma$-unsaturated nitrile-isomers occurs to a considerable extent in the decarboxylation of the alkylidene cyanoacetic acids prepared from cyanoacetic acid or esters and the oxo-compounds.

As the examples demonstrate, the nitriles of this invention exhibit a wide variety of odor effects. Many have woody character while others are musty and still others are floral or fruity in character. The nitriles of the invention can be used alone as fragrances per se or they can be used as components of a fragrance composition. The term "fragrance composition" is used to denote a mixture of compounds including, for example, natural oils, synthetic oils, alcohols, aldehydes, ketones, esters, lactones, ethers, hydrocarbons and other classes of chemical compounds which are admixed so that the combined odors of the individual components produce a pleasant or desired fragrance. Such fragrance compositions or the novel compounds of this invention can be used in conjunction with carriers, vehicles or solvents containing also, as needed, dispersants, emulsifiers, surface-active agents, aerosol propellants and the like.

In fragrance compositions the individual components contribute their particular olfactory characteristics, but the overall effect of the composition is the sum of the effect of each ingredient. Thus, the nitriles of this invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of nitrile which will be effective depends on many factors including the other ingredients, their amounts and the effects which are desired. It has been found that as little as 0.01 by weight of compounds of this invention can be used to alter the effect of a fragrance composition. The amount employed will depend on considerations of cost, nature of end product, the effect desired in the finished product, and the particular fragrance sought.

The compound disclosed herein can be used in a wide variety of applications such as, e.g., detergents and soaps; space deodorants-perfumes, colognes; after-shave lotions; bath preparations such as bath oil and bath salts; hair preparations such as lacquers; brilliantines, pomades and shampoos; cosmetic preparations such as creams, deodorants, hand lotions, and sun screens; powders such as talcs, dusting powders, face powder; as masking agents, e.g., in household products such as bleaches, and in technical products such as shoe polish and automobile wax.

EXAMPLE 1

A stirred mixture of 50 g (0.301 mole) formylcarane, obtained by hydroformylation of (+)-3-carene and consisting of about 70% 4-formylcarane and 30% 2-formylcarane, 26 g (0.306 mole) cyanoacetic acid, 1 g ammonium acetate, 60 ml pyridine and 200 ml toluene was refluxed for 65 hrs. in a three-necked round bottomed flask equipped with a Stark and Dean water trap. The theoretical amount (0.301 mole) of water was collected in the trap within 3 hrs. The mixture was poured into water and the organic material was extracted with ether. The combined ether layers were washed with water and dried with $Na_2SO_4$. Distillation yielded 45 g (0.238 moles=78%) of a mixture of isomers of 3-(3,7,7-trimethylbicyclo[4.1.0]heptyl-2 (and-4))acrylonitrile and 3-(3,7,7-trimethylbicyclo[4.1.0]heptylidene-2-(and-4)) propanenitrile, b.p. 92°-98° C. at 0.8 mm Hg, $n_D^{20}=1.4945$.

The mixture of nitrile isomers exhibited a strong, woody-angelica root, rosy, musky, carrots, lateron rosy sandalwood, cistus, labdanum odour. Dry out - strong sandalwood, cistus.

The nitrile mixture was separated via liquid chromatography in combination with preparative gas-liquid chromatography. Liquid chromatography conditions: prepacked silica gel columns 30 cm × 2.5 cm deactivated with 10-50% water saturated diethyl ether, mobile phase - normal pentane with 3% diethyl ether, room temperature, refractive index detector, using recycling where necessary. Gas-liquid chromatography conditions: 5 meter ×5 mm glass columns packed with Triton X305 supported on Chromosorb G AW DMCS mesh 80-100, column temperature 180° C., Pye 105 gaschromatograph.

Eight components of the mixture were separated and subjected to

IR and NMR spectroscopy and to odour evaluation. Two other components were separated in amounts sufficient for IR spectroscopy only.

Component 1

IR (in $CCl_4$), $cm^{-1}$: 3020 (sh), 2990, 2950, 2920, 2860, 2220 (m), 1617 (m), 1455 (m), 1371 (m), 1129 (w), 1102 (w), 1012 (m), 952 (w), 876 (w), 694 (w).

NMR (in $CCl_4$), $\delta$ of characteristic absorptions in ppm against TMS as internal standard: 0.47 (m, 1H, three-membered ring proton), 1.05 (s, 3H), 1.10 (s, 3H), 5.27 (d, 1H, J=10.5 Hz), 6.39 (t, J=10.5 Hz). Odor: weak with woody, musty and dung aspects.

Component 2

IR (in $CCl_4$), $cm^{-1}$: 3030 (sh), 2995, 2960, 2920, 2860, 2220 (m), 1620 (m), 1456 (m), 1374 (m), 1225 (w), 1170 (w), 1150 (w), 1130 (w), 1105 (w), 1015 (m), 954 (w), 876 (w), 698 (w).

NMR (in $CCl_4$), $\delta$ of characteristic absorptions in ppm against TMS as internal standard: 0.60 (m, 1H three-membered ring proton), 1.02 (s, 3H), 1.06 (s, 3H), 5.21 (d, 1H, J=10.5 Hz), 6.12 (t, 1H, J=10.5 Hz). Odor: weak woody, rosy.

Component 3

IR (in $CCl_4$), $cm^{-1}$: 3045, 2995, 2955, 2935, 2920, 2865, 2230 (m), 1631 (m), 1455 (m), 1374 (m), 1310 (w), 1236 (w), 1206 (w), 1170 (w), 1145 (w), 1132 (w), 1112 (w), 1096 (w), 1087 (w), 1015 (w-m), 970 (m), 940 (w), 890 (w), 850 (w), 695 (w).

NMR (in $CCl_4$), $\delta$ of characteristic absorptions in ppm against TMS as internal standard. 0.52 (m, 2H), 0.96 (s, 3H), 1.02 (s, 3H), 5.26 (d, 1H, J=16.5 Hz), 6.63 (dd, 1H, J=16.5 Hz and J=8.2 Hz). Odor: clear petitgrain, pyrazine-like.

Component 4

IR (in $CCl_4$), $cm^{-1}$; 3040 (sh), 2990, 2955, 2925, 2865, 2250 (w-m), 1643 (w-m) 1453 (m), 1430 (w), 1417 (m), 1375 (m), 1365 (w), 1310 (w), 1282 (w), 1273 (w), 1260 (w), 1230 (w), 1116 (w-m), 1089 (w), 1046 (w-m), 1016 (w-m) 990 (w-m), 950 (w-m), 915 (w-m).

NMR (in $CCl_4$), δ of characteristic absorption in ppm against TMS as internal standard. 0.91 (s, 3H), 1.19 (s, 3H), 3.02 (d, 2H, J=7.5 Hz), 5.31 (t, 1H). Odor: weak, woody, musty, rosy.

Component 5

IR (in $CCl_4$), $cm^{-1}$: 3045 (w), 2990, 2920, 2885, 2860, 2225 (m), 1633 (m), 1456 (m), 1439 (m), 1374 (m), 1303 (w), 1220 (w), 1174 (w), 1135 (w), 1118 (w), 1014 (w), 978 (m), 968 (m), 956 (m), 924 (w), 894 (w), 830 (w).

NMR (in $CCl_4$), δ of characteristic absorption in ppm against TMS as internal standard. 0.93 (s, 3H), 1.00 (s, 3H), 5.20 (d, 1H), J=16.5 Hz), 6.40 (m, 1H). Odor: strong rosy, orris, cuminic.

Component 6

IR (in $CCl_4$), $cm^{-1}$: 3030 (sh), 2990, 2960, 2930, 2865, 2245 (w), 1646 (w), 1452 (m), 1412 (w), 1374 (m), 1252 (w), 1210 (w), 1140 (w), 1116 (w), 972 (w), 950 (w), 918 (w).

NMR (in $CCl_4$), δ of characteristic absorption in ppm against TMS as internal standard. 0.88 (s, 3H), 1.02 (d, 3H, J=6, Hz), 1.16 (s, 3H), 3.03 (d, 2H, J=6 Hz), 5.40 (t, 1H). Odor: weak, woody, tobacco, rosy.

Component 7

IR (in $CCl_4$), $cm^{-1}$: 3060 (w), 2940, 2920, 2865, 2250 (w), 1660 (w), 1460 (m), 1435 (w—m), 1415 (w—m), 1375 (m), 1155 (w), 1123 (w), 1055 (w), 1018 (w), 920 (w—m), 702 (w).

NMR (in $CCl_4$), δ of characteristic absorption in ppm against TMS as internal standard. 0.63 (m, 2H), 3-membered ring protons), 1.05 (s, 6H), 3.05 (d, 2H, J=6.75 Hz), 5.20 (t, 1H). Odor: rosy, woody.

Component 8

IR (in $CCl_4$), $cm^{-1}$: 3060 (w), 2995, 2955, 2860, 2250 (w—m), 1652 (w), 1450 (m), 1425 (m), 1415 (sh), 1371 (m), 1235 (w), 1185 (w), 1125 (w), 1095 (w), 1010 (w), 985 (w), 955(w), 915 (w—m), 886 (w), 680 (w), 560 (w).

NMR (in $CCl_4$), δ of characteristic absorption in ppm against TMS as internal standard. 0.83 (s, 3H), 0.99 (s, 3H), 1.01 (d, 3H, J=6 Hz), 2.98 (d, 2H, J=6.75 Hz), 5.0 (t, 1H). Odor: strong sandalwoody, rosy.

Component 9

IR (in $CCl_4$), $cm^{-1}$: 2990, 2950, 2920, 2865, 2245, 1638 (w), 1464 (m), 1422 (m), 1372 (m), 1226 (w), 1129 (w), 1104 (w), 1026 (w), 960 (w), 950 (w), 913 (w), 890 (w), 695 (w).

Component 10

IR (in $CCl_4$), $cm^{-1}$: 3040 (sh), 2995, 2950, 2920, 2860, 2250 (w—m, 1640 (w—m), 1450 (m), 1416 (m), 1373 (m), 1215 (w), 1114 (w—m), 1085 (w), 1040 (w), 1014 (w), 955 (w), 931 (w), 916 (w), 896 (w), 865 (w), 691 (w).

The example demonstrates the wide variety of odor effects which are exhibited by the various nitriles of this invention individually and collectively.

EXAMPLE 2

A mixture of 20 g (0.120 mole) formylcarane, isomeric mixture as in Example 1, 11.3 g (0.133 mole) cyanoacetic acid, 0.4 g (0.0052 mole) ammonium acetate and 100 ml N,N-dimethylformamide was refluxed for five hours. After removal of the solvent by means of a rotatory evaporator, the residue was taken up in ether, washed with saturated $KHCO_3$ solution and saturated NaCl solution respectively, and dried with $Na_2SO_4$. After evaporation of the ether, distillation of the residue yielded 15 g (0.079 mole=66%) of the isomeric nitrile mixture, b.p. 100–101° C. at 0.8 mm Hg, $n_D^{20}$=1.4932, with odour and isomer distribution very similar to those of Example 1.

EXAMPLE 3

A mixture of 20 g (0.120 mole) formylcarane, isomeric mixture as in Example 1, 10.4 g (0.122 mole) cyanoacetic acid, 0.5 g (0.0065 mole) ammonium acetate and 100 ml toluene was refluxed with azeotropic removal of the water formed. After the theoretical amount of water was collected, the toluene was distilled off, the residue taken up in ether and extracted with 5% NaOH solution. The alkaline extractions were washed with saturated NaCl solution and dried with $Na_2SO_4$. Evaporation of the ether yielded 28 g of 2-cyano-3-(3,7,7-trimethylbicyclo[4.1.0]heptyl-2(and-4))acrylic acids.

(A) 10 g (0.043 mole) of this acid was dissolved in 50 ml N,N-dimethylformamide and refluxed for five hours. The solvent was then removed by means of a rotatory evaporator and the residue was taken up in ether, washed with saturated $KHCO_3$ solution and saturated NaCl solution respectively and dried with $Na_2SO_4$. After evaporation of the ether the residue was distilled and yielded 4.5 g (0.028 mole =65%) of the nitrile mixture, b.p. 105°–110° C. at 1 mm Hg, $n_D^{20}$=1.4939, with an odour pattern and isomer distribution very similar to those of Example 1.

(B) 7 g (0.030 mole) of the above prepared acids was mixed with 5.3 g (0.036 mole) triethanolamine. Distillation of the mixture at reduced pressure yielded 2.1 g (0.011 mole=37%) of the nitrile mixture, b.p. 92°–96° C. at 0.5 mm Hg, $n_D^{20}$ =1.4932, with rosy, woody odour.

(C) 14 g (0.060 mole) of the above prepared acids was mixed with 0.5 g (0.0035 mole) $Cu_2O$ and distilled at reduced pressure. Yield 10 g (0.053 mole=88%) of the nitrile mixture with woody rosy odour and somewhat higher content of component 2 of Example 1, b.p. 98°–101° C. at 0.9 mm, $n_D^{20}$ =1.4920.

EXAMPLE 4

A mixture of 10 g (0.060 mole) formylcarane, isomeric mixture as in Example 1, 6.8 g (0.060 mole) ethyl cyanoacetate, 0.5 g (0.0065 mole) ammonium acetate and 50 ml benzene was refluxed with azeotropic removal of the water formed. After the theoretical amount of water was collected, the benzene was distilled off, the residue taken up in ether, washed with water and dried with $Na_2SO_4$. After evaporation of the ether, distillation of the residue yielded 10 g (0.038 mole=64%) of ethyl 2-cyano-3-(3,7,7-trimethylbicyclo[4.1.0]heptyl-2(and-4))acrylates, b.p. 129°–132° C. at 0.7 mm Hg, $n_D^{20}$=1.4928. 9 g (0.034 mole) of this mixture was saponified with 2 g KOH (0.036 mole) in 10 ml ethanol during ten minutes. After evaporation of the ethanol, the residue was taken up in ether and washed with ether. The water layer was acidified with concentrated hydrochloric acid to pH=2 and the organic material was taken up in ether, washed with saturated NaCl solution and dried with $Na_2SO_4$. Evaporation of the ether yielded 8 g of crude acid which was decarboxylated by refluxing in dimethylformamide. Yield 4 g (0.021 mole=62%) isomeric nitrile mixture, b.p.

97°-98° C. at 0.7 mm Hg, $n_D^{20}$ =1.4939, with odour profile and isomer distribution similar to Example 1.

EXAMPLE 5

A mixture of 10 g (0.038 mole) of the ethyl 2-cyano-3-(3,7,7-trimethylbicyclo [4.1.0]heptyl-2(and-4))acrylates prepared in Example 4, 0.75 g (0.013 mole) NaCl, 1.4 g water (0.078 mole) and 40 ml N,N-dimethylformamide was refluxed for four hours. The reaction mixture was then poured into 400 ml water and the organic material was extracted with ether. The combined ether layers were washed with saturated NaCl solution and dried with $Na_2SO_4$. After evaporation of the ether, distillation of the residue yielded 3 g (0.016 mole=42%) of isomeric nitrile mixture with a higher content of component 8 to Example 1, and sandalwoody, rosy odour, b.p. 95°-98° C. at 0.6 mm Hg, $n_D^{20}$=1.4931.

EXAMPLE 6

A mixture of 20 g (0.120 mole) formylcarane, isomeric mixture as in Example 1, 13.6 g (0.120 mole) ethyl cyanoacetate, 0.7 g (0.012 mole) acetic acid and 75 ml dioxan was cooled to 0° C. and 1 ml piperidine was added dropwise. After stirring for an additional 10 minutes, 1 g 10% palladium on charcoal was added and the resulting mixture was hydrogenated at room temperature at normal pressure until the theoretical amount of hydrogen was taken up. The catalyst was removed by filtration and after evaporation of the solvent, the mixture was taken up in ether, washed with water, dilute hydrochloric acid, saturated $KHCO_3$ solution and saturated NaCl solution respectively and dried with $Na_2SO_4$. Distillation after evaporation of the ether yielded 24 g (0.091 mole =76%) ethyl 2-cyano-3-(3,7,7-bicyclo [4.1.0]heptyl-2(and-4)) propionate, b.p. 129°-131° C. at 0.6 mm Hg, $n_D^{20}$ =1.4725, which was saponified by stirring for 5 minutes at room temperature with 5.1 g KOH (0.091 mole) in 17 ml 96% ethanol. The ethanol was evaporated and the residue taken up in water and washed with ether. The water layer was acidified with hydrochloric acid to pH=2 and the organic material was taken up in ether, washed with saturated NaCl solution and dried with $Na_2SO_4$. After evaporation of the ether, the residue taken up in 50 ml N,N-dimethylformamide and decarboxylated and worked up as in Example 3A. Obtained was 12 g (0.063 mole=69%) 3-(3,7,7-trimethylbicyclo [4.1.0]heptyl-2 (and-4)) propanenitrile, b.p. 96°-98° C. at 0.6 mm Hg, $n_D^{20}$=1.4750, with weak woody, rosy odour.

EXAMPLE 7

To a suspension of 1.5 g (0.050 mole) 80% sodium hydride in 40 ml N,N-dimethylformamide was added dropwise during a half hour and in a nitrogen atmosphere a solution of 9 g (0.034 mole) ethyl 2-cyano-3-(3,7,7-trimethylbicyclo [4.1.0]heptyl-2 (and-4)) acrylates, prepared as in Example 4, in 10 ml N,N-dimethylformamide. The reaction temperature was kept at 40° C. for four more hours. Then 7.2 g (0.051 mole) of methyl iodide in 10 ml N,N-dimethylformamide was added in 15 minutes at 30° C. and the reaction mixture was stirred at room temperature for 60 hours and worked up, saponified and decarboxylated as in Example 4. Obtained was 4 g (0.020 mole =58%) mixture of 2-methyl-3-(3,7,7-trimethylbicyclo [4.1.0]heptylidene-2 (and-4) propanenitrile and 2-methyl-3-(3,7,7-trimethylbicyclo [4.1.0]heptyl-2 (and-4) acrylonitrile, b.p. 80°-82° C. at 0.3 mm Hg, $n_D^{20}$=1.4869, with floral, rosy, woody odour.

EXAMPLE 8

The nitrile mixture 2-ethyl-3-(3,7,7-trimethylbicyclo [4.1.0]heptylidene-2 (and-4))propanenitrile and 2-ethyl-3-(3,7,7-trimethylbicyclo [4.1.0]heptyl-2and-4))acrylonitrile was prepared according to the procedure ot Example 7 with ethyl bromide instead of methyl iodide. Obtained was 56% product of b.p. 100°-102° C. at 0.5 mm Hg, $n_D^{20}$=1.4870, with musty, fruity, woody odour.

EXAMPLE 9

The nitrile mixture 2-n-butyl-3-(3,7,7-trimethylbicyclo [4.1.0]heptylidene-2 (and-4))propanenitrile and 2-n-butyl-3-(3,7,7-trimethylbicyclo [4.1.0]heptyl-2 (and-4))acrylonitrile was prepared according to the procedure of Example 7 with n-butyl bromide instead of methyl iodide. Yield 38%, b.p. 111°-113° C. at 0.4 mm Hg, $n_D^{20}$=1.4888, with animalic, woody odour.

EXAMPLE 10

A mixture of 2-n-hexyl-3-(3,7,7-trimethylbicyclo [4.1.0]heptylidene-2 (and-4))propanenitrile and 2-nhexyl-3-(3,7,7-trimethylbicyclo [4.1.0]heptyl-2 (and-4))acrylonitrile was prepared according to the procedure of Example 7 with n-hexylbromide instead of methyl iodide. Yield 33%, b.p. 140°-142° C. at 0.3 mm Hg, $n_D^{20}$=1.4812, with weak jasminic, woody odour.

EXAMPLE 11

To a suspension of 1.8 g 80% NaH (0.060 mole) in 100 ml N,N-dimethylformamide in a nitrogen atmosphere was added dropwise during 30 minutes 10.7 g (0.060 mole) diethyl cyanomethylphosphonate, while the temperature was kept below 32° C. After the addition was complete the reaction was kept at 30° C. for 15 minutes and then 10 g formylcarane (0.060 mole), isomeric mixture as in Example 1, was added dropwise in the course of 15 minutes. The reaction temperature rose to 40° C. and was kept at 40-45° C. for two more hours. After cooling to room temperature 10 g acetic acid was added, the solvent removed by distillation and the residue taken up in ether and washed with water, saturated $KHCO_3$ solution, saturated NaCl solution and dried with $Na_2SO_4$. Distillation yeilded 9 g (0.048 mole =79%) of predominantly 3-(3,7,7-trimethylbicyclo [4.1.0]heptyl-2 (and-4))acrylonitrile and of 3-(3,7,7-trimethylbicyclo [4.1.0]heptylidene-2 (and-4))propanenitrile, with woody, orrisy odour, b.p. 85-87° C. at 0.8 mm Hg, $n_D^{20}$=1.4932.

EXAMPLE 12

To a mixture of 10 g (0.060 mole) formylcarane, isomeric mixture as in Example 1, 10.7 g (0.060 mole) diethyl cyanomethylphosphonate and 75 ml methanol was added dropwise in the course of 35 minutes at 0° C. a solution of 3 g (0.075 mole) sodium hydroxide in 20 ml water. The mixture was stirred for 2¼ hours during which period the temperature was allowed to rise to 20° C. Then successively were introduced 10 ml acetic acid with cooling and 100 ml water. The water layer was extracted twice with ether and the combined ether layers were washed with saturated $KHCO_3$ solution and saturated NaCl solution and dried with $Na_2SO_4$. Distillation yielded 9.6 g (0.051 mole=85%) of the nitrile mixture with odour and isomer distribution very similar to those of Example 11, b.p. 94°-95° C. at 0.8 mm Hg, $n_D^{20}=1.4955$.

EXAMPLE 13

To a solution of 19.3 g (0.060 mole) tetrabutylammonium bromide in 150 ml 0.5 N NaOH was added at once a mixture of 10 g (0.060 mole) formylcarane, isomeric mixture as in Example 1, 11.5 g (0.060 mole) diethyl 1-cyanoethylphosphonate and 150 ml methylenechloride, and the mixture was stirred vigourously for 3 hours. The temperature initially rose to 26° C. and was allowed to drop to room temperature again in the course of the reaction. The organic layer was separated and the solvent was removed by evaporation. The residue was taken up in ether and dried with $Na_2SO_4$. After filtration the ether was evaporated. Distillation of the residue yielded 9.6 g (0.047 mole =79%) isomeric mixture of predominantly 2-methyl-3-(3,7,7-trimethylbicyclo [4.1.0]heptyl-2(and-4)) acrylonitrile and of 2-methyl-3-(3,7,7-trimethylbicyclo [4.1.0]heptylidene-2 (and-4))propanenitrile, b.p. 95°-100° C. at 1 mm Hg, $n_D^{20}=1.4870$, with fatty woody odour.

EXAMPLE 14

Analogously to Example 11 was prepared 2-n-butyl-3-(3,7,7-trimethylbicyclo [4.1.0]heptyl-2 (and-4))acrylonitrile from formylcarane, isomeric mixture as in Example 1, and diethyl 1-cyanopentylphosphonate in 71% yield, with weak, woody odour, b.p. 95°-100° C. at 0.05 mm Hg, $n_D^{20}=1.4831$.

EXAMPLE 15

The condensation of cyanoacetic acid and 4-formylcarane obtained via the Prins reaction of 3-carene as described in Annalen 613, p. 43 (1958), was carried out according to the procedure of Example 3A. Yield 73% of the isomeric mixture 3-(3,7,7-trimethylbicyclo [4.1.0]heptylidene-4)propanenitrile and 3-(3,7,7-trimethylbicyclo [4.1.0]heptyl-4)acrylonitrile, b.p. 99°-103° C. at 0.6 mm Hg, $n_D^{20}=1.4950$, with metallic, woody, rosy odour.

EXAMPLE 16

The procedure of Example 6 was carried out with the same starting material as in Example 15. Obtained was 50% overall yield of 3-(3,7,7-trimethylbicyclo [4.1.0]heptyl-3)propanenitrile, with watery, metallic, woody odour, b.p. 91°-92° C. at 0.5 mm Hg, $n_D^{20}=1.4751$.

EXAMPLE 17

The reaction of Example 11 was carried out with the same starting material as in Example 15. Obtained was 50% isomeric mixture of predominantly 3-(3,7,7-trimethylbicyclo [4.1.0]heptylidene-4)propanenitrile with fatty, woody odour, b.p. 95°-98° C. at 1.2 mm Hg, $n_D^{20}=1.4921$.

EXAMPLE 18

An isomeric mixture of predominantly 3-(3,7,7-trimethylbicyclo [4.1.0]-2-heptenyl-4)-2-butenenitrile with fatty, woody, myrrhlike, cuminic odour was prepared in 73% yield from 4-acetyl-3,7,7-trimethylbicyclo 4.1.0]-2-heptene and diethyl cyanomethylphosphonate according to the procedure of Example 11, b.p. 86°-90° C. at 0.2 mm Hg, $n_D^{20}=1.5120$.

EXAMPLE 19

According to the procedure of Example 11 was prepared 3-(3,7,7-trimethylbicyclo [4.1.0]heptyl-4)-2-butenenitrile from 4-acetyl-3,7,7-trimethylbicyclo [4.1.0]heptane and diethyl cyanomethylphosphonate in 44% yield, with fatty earthy, woody odour, b.p. 88°-91° C. at 0.5 mm Hg, $n_D^{20}=1.4969$.

EXAMPLE 20

Analogously to Example 11 was prepared 2-methyl-3-(3,7,7-trimethylbicyclo [4.1.0]heptyl-4)-2-butenenitrile from 4-acetyl-3,7,7-trimethylbicyclo [4.1.0]heptane and diethyl 1-cyanoethylphosphonate in 47% yield with phenolic, woody, mossy odour, b.p. 105°-111° C. at 0.7 mm Hg, $n_D^{20}=1.4951$.

EXAMPLE 21

A mixture of 5 g (0.028 mole) 4-acetyl-3,7,7-trimethylbicyclo [4.1.0]heptane, 1.9 g KOH (85%, 0.029 mole) and 20 g acetonitrile was refluxed for 20 hours. The cooled mixture was mixed with 50 ml water and 2 ml acetic acid and extracted with ether. The ether layers were washed with saturated $KHCO_3$ solution and saturated NaCl solution and dried with $Na_2SO_4$. Distillation yielded 7% of the isomeric mixture 3-(3,7,7-trimethylbicyclo [4.1.0]heptyl-4)-2-butenenitrile and 3-(3,7,7-trimethylbicyclo [4.1.0]heptylidene-4)butanenitrile, with odour similar to Example 19, b.p. 96°-98° C. at 0.5 mm Hg.

EXAMPLE 22

Analogously to Example 11 was prepared 3-(3,7,7-trimethylbicyclo [4.1.0]-3-heptenyl-2)-2-butenenitrile from 2-acetyl-3,7,7-trimethylbicyclo [4.1.0]-3-heptene and diethyl cyanomethylphosphonate in 71% yield with woody, orangy odour, b.p. 84°-86° C. at 0.5 mm Hg, $n_D^{20}=1.5095$.

EXAMPLE 23

Analogously to Example 11 was prepared 2-methyl-3-(3,7,7-trimethylbicyclo [4.1.0]-3-heptenyl-2)-2-butenenitrile from 2-acetyl-3,7,7-trimethylbicyclo [4.1.0]-3-heptene and diethyl 1-cyanoethylphosphonate in 43% yield with ambery, woody odour, b.p. 100°-102° C. at 0.7 mm Hg, $n_D^{20}=1.5095$.

EXAMPLE 24

Analogously to Example 11 was prepared 3-(3,7,7-trimethylbicyclo [4.1.0]heptyl-2)-2-butenenitrile from 2-acetyl-3,7,7- trimethylbicyclo [4.1.0]heptane and diethyl cyanomethylphosphonate in 57% yield with metallic, cinnamic, woody odour, b.p. 95°-100° C. at 0.9 mm Hg, $n_D^{20}=1.4971$.

EXAMPLE 25

Analogously to Example 11 was prepared 2-methyl-3-(3,7,7-trimethylbicyclo [4.1.0]heptyl-2)-2-butenenitrile from 2-acetyl-3,7,7-trimethylbicyclo [4.1.0]heptane and diethyl 1-cyanoethylphosphonate 26% yield with minty, woody odour, b.p. 110°-115° C. at 0.7 mm Hg, $n_D^{20}=1.4959$.

EXAMPLE 26

Analogously to Example 11 was prepared 3-(3,7,7-trimethylbicyclo [4.1.0]-2-heptenyl-4)-2-pentenenitrile from 4-propionyl-3,7,7-trimethylbicyclo [4.1.0]-2-heptane and diethyl cyanomethylphosphonate in 47% yield, with soupy, woody, odour, b.p. 110°-115° C. at 0.5 mm Hg, $n_D^{20}$1.5051.

EXAMPLE 27

Analogously to Example 11 was prepared 2-methyl-3-(3,7,7-trimethylbicyclo [4.1.0]-2-heptenyl-4)-2-penenenitrile from 4-propionyl-3,7,7-trimethylbicyclo [4.1.0]-2-heptene and diethyl 1-cyanoethylphosphonate in 21% yield, with musty, woody odour, b.p. 100°-110° C. at 0.6 mm Hg, $n_D^{20}=1.5089$.

EXAMPLE 28

Analogously to Example 11 was prepared 3-(3,7,7-trimethylbicyclo[4.1.0]heptyl-4)-2-pentenenitrile from 4-propionyl-3,7,7-trimethylbicyclo [4.1.0]heptane and diethyl cyanomethylphosphonate in 33% yield, with rosy, cuminic odour, b.p. 110°-115° C. at 0.7 mm Hg, $n_D^{20}=1.4959$.

EXAMPLE 29

A perfume composition is produced by admixing the following ingredients:

250 hydroxycitronellal
180 bergamot oil
100 musk ambrette
40 benzoin resinoid siam
40 benzyl benzoate
80 2-hexyl-3-carbomethoxycyclopentanone
50 4-(and 3-) (4-hydroxy-4-methylpentyl)-3-cyclohexenecarbaldehyde
50 ε-methylionone
40 α-amylcinnamic aldehyde
20 patchouli oil
20 geranium oil (Bourbon)
20 ylang ylang oil, first quality
20 petit grain oil (Paraquay)
10 verbena oil
10 oakmoss absolute
10 heliotropine
10 cumarine
50 isomeric nutrile mixture of Example 1

The addition of the isomeric mixture of Example 1 gives the composition the desired richness as well as in the top as in the dry-out.

EXAMPLE 30

A perfume composition is produced by admixing the following ingredients:

275 bergamot oil
50 lavender oil
150 lemon oil (Sicilian)
75 cedarwood oil
75 vetiver oil
75 γ-methylionone
60 isoamyl salicylate
30 ylang ylang oil, first quanlity
30 geranium oil (Bourbon)
75 musk ketone
45 musk ambrette
5 grisambrol (Firmenich)
3 methylnonylacetaldehyde
2 undecylenic aldehyde
150 nitrile prepared according to Example 20

The addition of the nitrile prepared according to Example 20 gives a strong rounding-off effect to the woody aspects of the composition, which declares itself especially in the dry-out.

EXAMPLE 31

A perfume composition is prepared by admixing the following ingredients:

75 orange oil
75 lemon oil
150 bergamot oil
150 hydroxycitronellal
60 γ-methylionone
45 cumarine
60 geraniol
45 clary sage oil
65 celestolide (IFF)
45 musk ambrette
30 vetiver oil
25 geranium oil (Bourbon)
20 ylang ylang oil
30 patchouli oil
2 undecylenic aldehyde
3 styrallyl acetate
120 nitrile prepared according to Example 23

Addition of the nitrile of Example 23 gives the desired richness to the body of the composition, but also a (unexpected) lift of the citrusy top-odours.

What is claimed is:

1. A compound selected from the class of compounds having the structural formulae

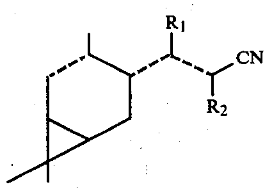
(a)

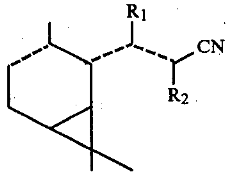
(b)

wherein $R_1$ and $R_2$ are hydrogen or alkyl groups of 1 to 6 carbon atoms and the total carbon number of $R_1$ and $R_2$ combined is 6 or less and the dotted lines indicate carbon to carbon double or single bonds with the further provised that only one such bond is present in the side chain.

2. A compound of claim 1 having the basic structural formula

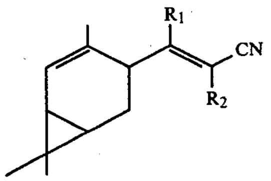

3. A compound of claim 1 having the basic structural formula

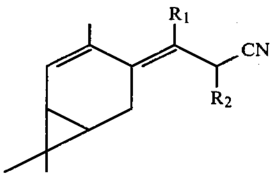

4. A compound of claim 1 having the basic structural formula

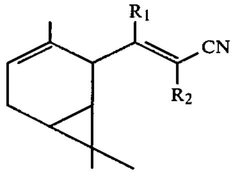

5. A compound of claim 1 having the basic structural formula

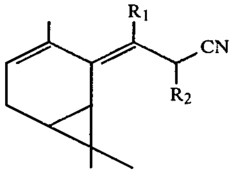

6. A compound of claim 1 having the basic structural formula

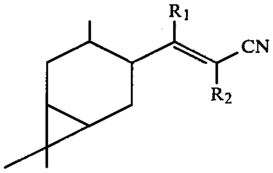

7. A compound of claim 1 having the basic structural formula

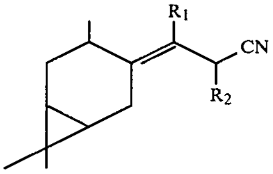

8. A compound of claim 1 having the basic structural formula

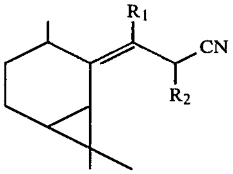

9. A compound of claim 1 having the basic structural formula

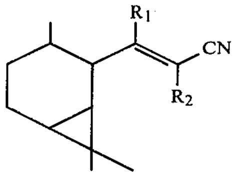

10. A compound of claim 1 having the basic structural formula

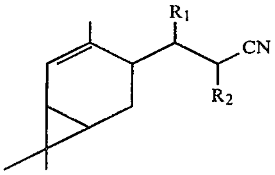

11. A compound of formula 1 having the basic structural formula

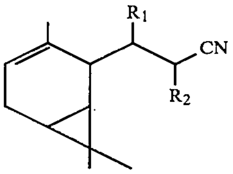

12. A compound of claim 1 having the basic structural formula

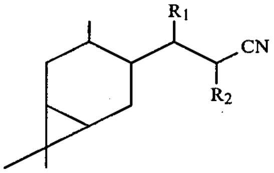

13. A compound of claim 1 having the basic structural formula

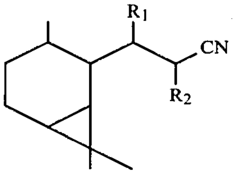

14. A mixture of two or more chemical compounds having basic structural formulae selected from the class consisting of

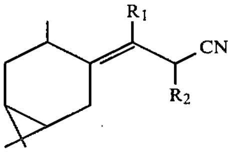

(1)

-continued

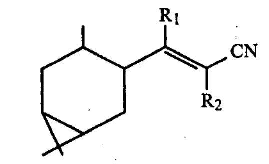

(2)

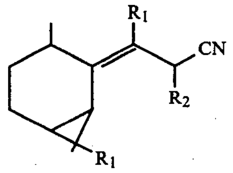

and (3)

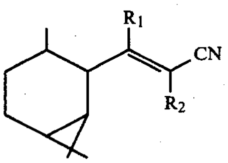

(4)

where $R_1$ and $R_2$ represent hydrogen or alkyl radicals having 1 to 6 carbon atoms and the total carbon number of $R_1$ and $R_2$ is 6 or less.

15. A mixture of two or more chemical compounds having basic structural formulae selected from the class consisting of

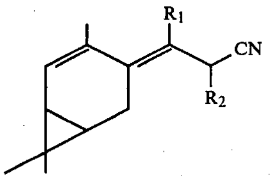

(1)

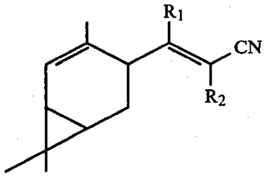

(2)

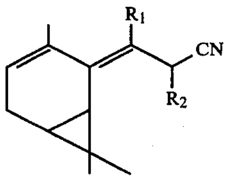

and (3)

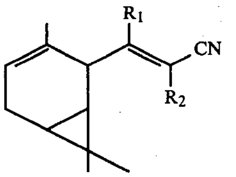

(4)

where $R_1$ and $R_2$ represent hydrogen or alkyl radicals having 1 to 6 carbon atoms and the total carbon number of $R_1$ and $R_2$ is 6 or less.

16. A chemical compound having the structural formula

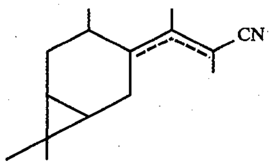

where the dotted lines represent a single carbon to carbon double bond.

17. A chemical compound having the structural formula

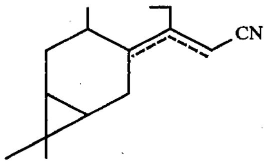

where the dotted lines represent a single carbon to carbon double bond.

18. A chemical compound having the structural formula

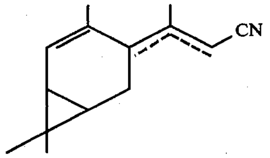

where the dotted lines represent a single carbon to carbon double bond.

19. A chemical compound having the structural formula

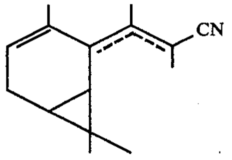

wherein the dotted lines represent a single carbon to carbon double bond.

20. A chemical compound having the structural formula

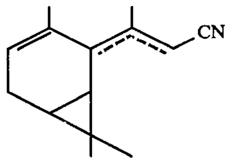

where the dotted line represents a single carbon to carbon double bond.

21. A chemical compound having the structural formula

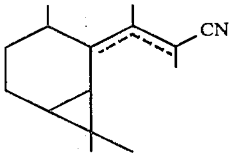

where the dotted line represents a single carbon to carbon double bond.

22. A chemical compound having the structural formula

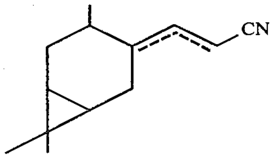

where the dotted line represents a single carbon to carbon double bond.

23. A chemical compound having the structural formula

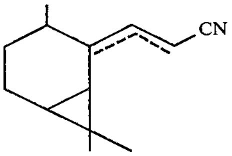

where the dotted line represents a single carbon to carbon doubl bond.

24. A perfume composition comprising, in admixture with other olfactorily active ingredients, at least one compound selected from the class of compounds having the structural formulae

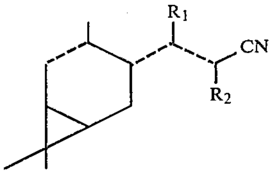
(a)

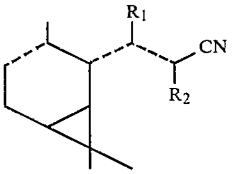
(b)

wherein $R_1$ and $R_2$ are hydrogen or alkyl groups of 1 to 6 carbon atoms and the total carbon number of $R_1$ and $R_2$ combined is 6 or less and the dotted lines indicate carbon to carbon double or single bonds with the further proviso that only one such bond is present in the side chain.

25. A perfume composition comprising, in admixture with other olfactorily active ingredients a mixture of 2 or more chemical compounds having basic structural formulae selected from the class consisting of

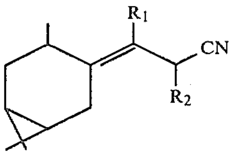
(1)

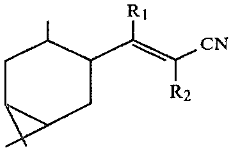
(2)

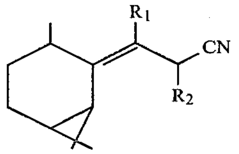
(3)

and

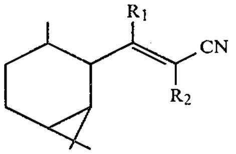
(4)

where $R_1$ and $R_2$ represent hydrogen or alkyl radicals having 1 to 6 carbon atoms and the total carbon number of $R_1$ and $R_2$ is 6 or less.

26. A perfume composition comprising, in admixture with other olfactorily active ingredients a mixture of 2 or more chemical compounds having basic structural formulae selected from the class consisting of

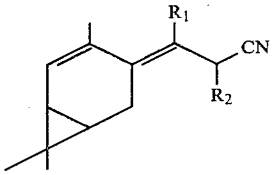
(1)

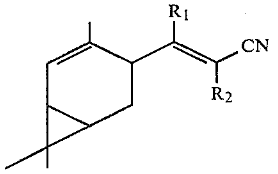
(2)

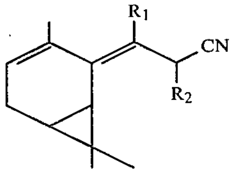
(3)

and

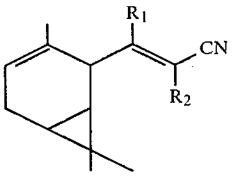
(4)

where $R_1$ and $R_2$ represent hydrogen or alkyl radicals having 1 to 6 carbon atoms and the total carbon number of $R_1$ and $R_2$ is 6 or less.

27. A perfume composition comprising, in admixture with other olfactorily active ingredients, a chemical compound having the structural formula

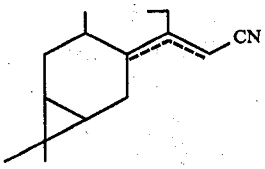

where the dotted lines represent a single carbon to carbon double bond.

28. A perfume composition comprising, in admixture with other olfactorily active ingredients, a chemical compound having the structural formula

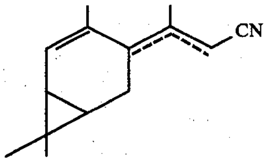

where the dotted lines represent a single carbon to carbon double bond.

29. A perfume composition comprising, in admixture with other olfactorily active ingredients, a chemical compound having the structural formula

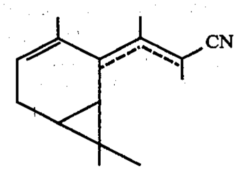

where the dotted lines represent a single carbon to carbon double bond.

30. A perfume composition comprising, in admixture with other olfactorily active ingredients, a chemical compound having the structural formula

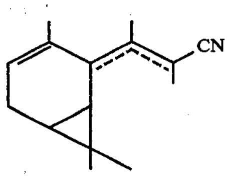

where the dotted lines represent a single carbon to carbon double bond.

31. A perfume composition comprising, in admixture with other olfactorily active ingredients, a chemical compound having the structural formula

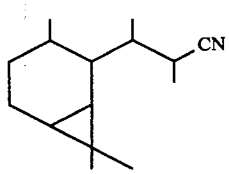

where the dotted lines represent a single carbon to carbon double bond.

32. A perfume composition comprising, in admixture with other olfactorily active ingredients, a chemical compound having the structural formula

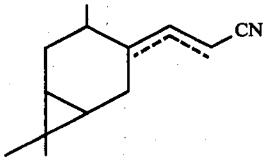

where the dotted lines represent a single carbon to carbon double bond.

33. A perfume composition comprising, in admixture with other olfactorily active ingredients, a chemical compound having the structural formula

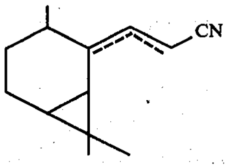

where the dotted lines represent a single carbon to carbon double bond.

34. A perfume composition comprising, in admixture with other olfactorily active ingredients, a chemical compound having the structural formula

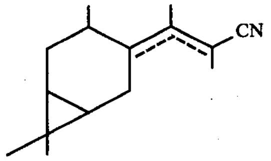

where the dotted lines represent a single carbon to carbon double bond.

35. A mixture of chemical compounds having the basic structural formulae

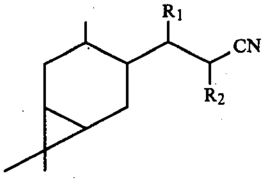 (1)

and

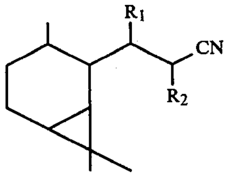 (2)

where $R_1$ and $R_2$ represent hydrogen or alkyl radicals of 1 to 6 carbon atoms and the total number of $R_1$ and $R_2$ is 6 or less.

36. A mixture of chemical compounds having the basic structural formulae

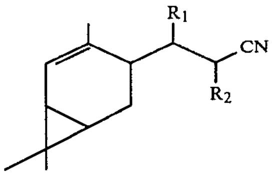
(1)
and

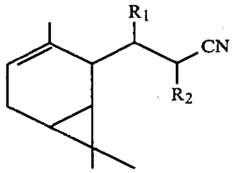

where $R_1$ and $R_2$ represent hydrogen or alkyl radicals of 1 to 6 carbon atoms and the total carbon number of $R_1$ and $R_2$ is 6 or less.

37. A perfume composition comprising, in admixture with other olfactorily active ingredients, a mixture of chemical compounds having the basic structural formulae

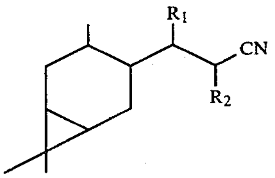
(1)
and

-continued

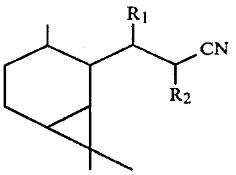
(2)

where $R_1$ and $R_2$ represent hydrogen or alkyl radicals of 1 to 6 carbon atoms and the total carbon number of $R_1$ and $R_2$ is 6 or less.

38. A perfume composition comprising, in admixture with other olfactorily active ingredients, a mixture of chemical compounds having the basic structural formulae

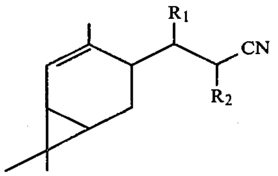
(1)
and

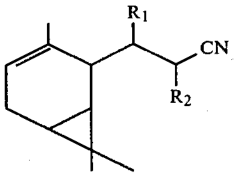
(2)

where $R_1$ and $R_2$ represent hydrogen or alkyl radicals of 1 to 6 carbon atoms and the total carbon number of $R_1$ and $R_2$ is 6 or less.

* * * * *

UNITED STATES PATENT AND TRADEMARK OFFICE

CERTIFICATE OF CORRECTION

PATENT NO. : 4,219,449

DATED : August 26, 1980

INVENTOR(S) : Willem Lenselink and Dirk K. Kettenes

It is certified that error appears in the above-identified patent and that said Letters Patent are hereby corrected as shown below:

Col. 2, line 45 " cyclonalkyl " should read -- cyanoalkyl --.

Col. 5 between lines 15 and 20, formula III,

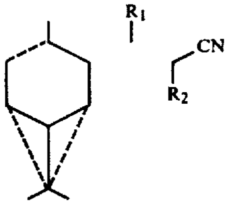

III should read

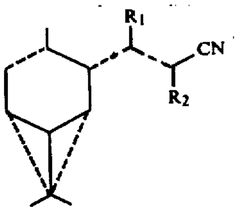

III

Col. 5, formula XI,

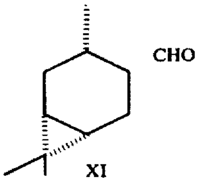

XI should read

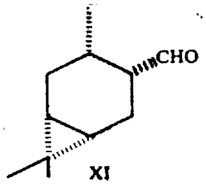

XI

UNITED STATES PATENT AND TRADEMARK OFFICE
CERTIFICATE OF CORRECTION

PATENT NO. : 4,219,449 Page 2 of 3

DATED : August 26, 1980

INVENTOR(S) : Willem Lenselink and Dirk K. Kettenes

It is certified that error appears in the above—identified patent and that said Letters Patent is hereby corrected as shown below:

Col. 7, lines 15 and 16 " enantiomorphs " should read -- enantiomorphic --.

Col. 7, lines 27 and 28 " enanthiomorphs " should read -- enantiomorphs --.

Col. 17, line 7 " pennenenitrile " should read -- pentenenitrile --1.

Col. 17, line 32 " 50 E- " should read -- 50 $\gamma$ --.

In the Claims, Col. 18, Claim 1, line 53 " provised " should read -- proviso --.

Col. 23, Claim 23, line 38 " doubl " should read -- double --.

UNITED STATES PATENT AND TRADEMARK OFFICE

CERTIFICATE OF CORRECTION

PATENT NO. : 4,219,449

DATED : August 26, 1980

INVENTOR(S) : Willem Lenselink and Dirk K. Kettenes

It is certified that error appears in the above—identified patent and that said Letters Patent is hereby corrected as shown below:

Col. 25, Claim 31 in the formula,

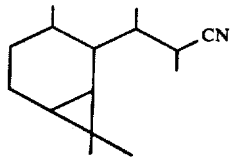

should read

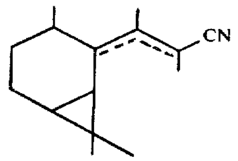

Signed and Sealed this

*Eleventh* Day of *November 1980*

[SEAL]

*Attest:*

SIDNEY A. DIAMOND

*Attesting Officer*

*Commissioner of Patents and Trademarks*